United States Patent [19]
Baudy et al.

[11] Patent Number: 5,602,128
[45] Date of Patent: Feb. 11, 1997

[54] N-HETEROCYCLOALKYL CARBOXAMIDES AS SEROTONERGIC AGENTS

[75] Inventors: Reinhardt B. Baudy, Yardley, Pa.; Scott C. Berta, N. Brunswick, N.J.

[73] Assignee: American Home Products Corporation, Madison, N.J.

[21] Appl. No.: 348,651

[22] Filed: Dec. 2, 1994

[51] Int. Cl.$^6$ .................. A61K 31/535; A61K 31/54; C07D 413/04; C07D 417/02
[52] U.S. Cl. .................. 514/227.8; 514/235.8; 514/252; 544/58.6; 544/121; 544/357
[58] Field of Search .................. 544/58.6, 121, 544/357; 514/227.8, 235.8, 252

[56] References Cited

U.S. PATENT DOCUMENTS

| | | | |
|---|---|---|---|
| 3,717,634 | 2/1973 | Hua et al. | 544/295 |
| 4,182,763 | 1/1980 | Casten et al. | 544/295 |
| 5,278,160 | 1/1994 | Abou-Gharbia et al. | 514/247 |
| 5,348,955 | 9/1994 | Greenlee et al. | 514/227.8 |

FOREIGN PATENT DOCUMENTS 2230781  10/1990  United Kingdom.

Primary Examiner—Matthew V. Grumbling
Attorney, Agent, or Firm—Richard K. Jackson

[57] ABSTRACT

The compounds

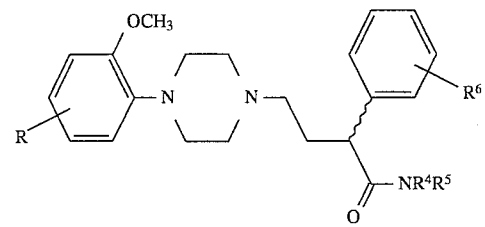

where R and $R^6$ are members independently selected from the group consisting of H, CN, $OR^2$, $NO_2$, $NR^2R^3$, $NR^2COR^3$, $NR^2COOR^3$, $COR^2$, $COOR^2$, $CONR^2R^3$, $SR^2$, $SOR^2$, $SO_2R^2$, $SO_2NR^2R^3$, alkyl, alkenyl, alkynyl, perhaloalkyl, and a halogen; in which $R^2$ and $R^3$ are alkyl, alkenyl, alkynyl, phenyl, or benzyl; $R^4$ is a member selected from the group consisting of H, alkyl, heteroalkyl, in which the hetero atom is oxygen, sulfur or nitrogen, alkenyl and alkynyl; $R^5$ is

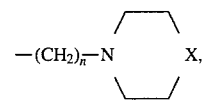

where X is O, S or $NR^7$ and $R^7$ is H or alkyl and n is 1, 2, 3, 4, 5, or 6; or a pharmaceutically acceptable salt thereof, are useful anxiolytic/antidepressant agents.

7 Claims, No Drawings

N-HETEROCYCLOALKYL CARBOXAMIDES AS SEROTONERGIC AGENTS

BACKGROUND OF THE INVENTION

Compounds having selectivity for the 5-HT$_{1A}$ receptor have established a domain in the marketplace as effective anxiolytic agents (buspirone, U.S. Pat. No. 3,717,634). In addition to the treatment of anxiety, selective 5-HT$_{1A}$ antagonists are also useful as mixed anxiolytic, antidepressant agents.

DESCRIPTION OF THE INVENTION

In accordance with this invention, there is provided a set of novel compounds including their enantiomers which have activity as serotonergic agents. Compounds of the present invention are described by the genetic formula:

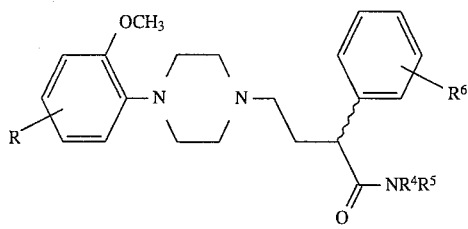

where:

R and R$^6$ are members independently selected from the group consisting of H, CN, OR$^2$, NO$_2$, NR$^2$R$^3$, NR$^2$COR$^3$, NR$^2$COOR$^3$, COR$^2$, COOR$^2$, CONR$^2$R$^3$, SR$^2$, SOR$^2$, SO$_2$R$^2$, SO$_2$NR$^2$R$^3$, alkyl of 1 to 6 carbon atoms, alkenyl of 2 to 6 carbon atoms, alkynyl of 2 to 6 carbon atoms, perhaloalkyl of 1 to 6 carbon atoms, and a halogen; in which R$^2$ and R$^3$ are alkyl of 1 to 6 carbon atoms, alkenyl of 2 to 6 carbon atoms, alkynyl of 2 to 6 carbon atoms, phenyl, or benzyl;

R$^4$ is a member selected from the group consisting of H, alkyl of 1 to 6 carbon atoms, heteroalkyl of 2 to 6 carbon atoms, in which the hetero atom is oxygen, sulfur or nitrogen, alkenyl of 2 to 6 carbon atoms and alkynyl of 2 to 6 carbon atoms;

R$^5$ is

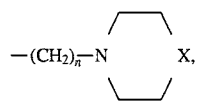

where X is O, S or NR$^7$ and R$^7$ is H or alkyl of 1 to 6 carbon atoms and n is 1, 2, 3, 4, 5, or 6;

or a pharmaceutically acceptable salt thereof.

Of these compounds, the preferred members are those in which R and R$^6$ are H, R$^4$ is H or alkyl of 1 to 6 carbon atoms and X is O or S and more preferably, R$^4$ is alkyl of 1 to 3 carbon atoms and X is O.

The pharmaceutically acceptable salts are those derived from such organic and inorganic acids as: acetic, lactic, citric, tartaric, succinic, maleic, malonic, hydrochloric, hydrobromic, phosphoric, nitric, sulfuric, methanesulfonic, and similarly known acceptable acids.

The compounds of this invention are prepared by conventional methods. For example, the appropriately substituted "acid" is transformed in the presence of a coupling agent like N,N-bis(2-oxo-3-oxazolidinyl)phosphoramidic chloride to yield the desired products (1).

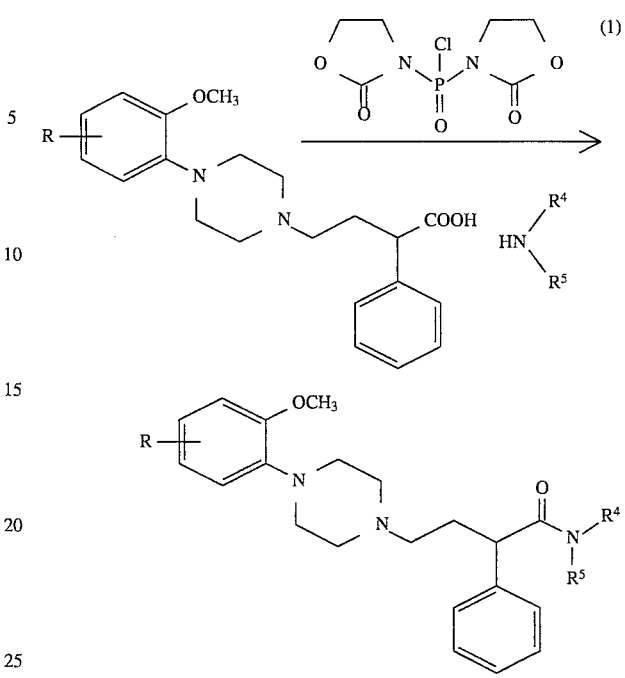

High affinity for the serotonin 5-HT$_{1A}$ receptor was established by testing the claimed compound's ability to displace [$^3$H] 8-OHDPAT (dipropylaminotetralin) from the 5-HT$_{1A}$ serotonin receptor following the procedure of Hall et al., J. Neurochem. 44, 1685(1985). This procedure is employed to analogize this property of the claimed compounds with that of buspirone, which is a standard for anxiolytic activity, and, like the compounds of this invention, displays potent affinity for the 5-HT$_{1A}$ serotonin receptor subtype. The anxiolytic activity of buspirone is believed to be, at least partially, due to its 5-HT$_{1A}$ receptor affinity (Vander Maclen et al., Eur. J. Pharmacol. 1986, 129 (1–2) 133-130).

The result of the standard experimental test procedure described in the preceding paragraph was as follows when applied to the representative compound of this invention:

| Compound | 5-HT$_{1A}$Binding (IC$_{50}$) |
| --- | --- |
| Example 1 | 95.2 nM |

Hence, the compounds of this invention demonstrate high affinity for the serotonin 5-HT$_{1A}$ receptor subtype, and are therefore useful in the treatment of multi-CNS disorders amenable to treatment with antidepressant and anxiolytic agents.

Based upon this receptor binding data, the compounds of this invention are characterized as anxiolytic and/or antidepressant agents useful in the treatment of depression and in alleviating anxiety. As such, the compounds may be administered neat or with a pharmaceutical carder to a patient in need thereof. The pharmaceutical carrier may be solid or liquid.

Applicable solid carriers can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carrier ha,,ring the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific patient suffering from depression or anxiety must be subjectively determined by the attending physician. The variables involved include the specific state of anxiety ore depression, and the size, age and response pattern of the patient.

The following examples illustrate the production of representative compounds of this invention.

EXAMPLE 1

4-[4-(2-Methoxy-phenyl)-piperazin-1-yl]-N-(2-morpholin-4-yl-ethyl)-2phenyl-butyramide A mixture of 4-[4-(2-methoxyphenyl)piperazin-1-yl]-2-phenylbutanoic acid (3.544 g, 10 mmole), triethylamine (2.024 g, 20 mmole), and N,N-bis(2-oxo-3oxazolidinyl)phosphoramidic chloride (2.545 g. 10 mmole) was stirred in methylene chloride (80 mL) under exclusion of moisture at ambient temperature for 30 minutes, after which 4-(2-aminoethyl)morpholine (1.302 g, 10 mmole) was added. The reaction mixture was stirred at room temperature for 14 hours, washed with water (100 ml), dried over magnesium sulfate, filtered and evaporated to dryness in vacuo. Chromatography on silica gel with methanol/chloroform as eluant, followed by crystallization from ethanol/diethyl ether with addition of ethanolic HCl gave 0.6 g of the title compound as the dihydrochloride, 2.5 hydrate, 0.2 CHCl₃ solvate, m.p. 60°–5° C.

Elemental Analysis for: $C_{27}H_{38}N_4O_3 \cdot 2HCl \cdot 2.5H_2O \cdot 0.2CHCl_3$ Calcd: C, 53.68; H, 7.48; N, 9.20

Found: C, 53.47; H, 7.06; N, 9.44

What is claimed is:

1. A compound of the formula:

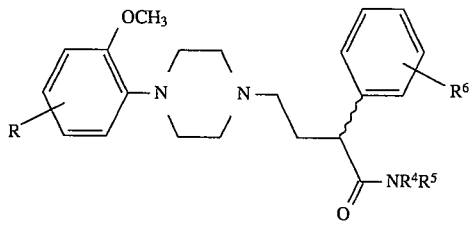

where:

R and $R^6$ are members independently selected from the group consisting of H, CN, $OR^2$, $NO_2$, $NR^2R^3$, $NR^2COR^3$, $NR^2COOR^3$, $COR^2$, $COOR^2$, $CONR^2R^3$, $SR^2$, $SOR^2$, $SO_2R^2$, $SO_2NR^2R^3$, alkyl of 1 to 6 carbon atoms, alkenyl of 2 to 6 carbon atoms, alkynyl of 2 to 6 carbon atoms, perhaloalkyl of 1 to 6 carbon atoms, and a halogen; in which $R^2$ and $R^3$ are alkyl of 1 to 6 carbon atoms, alkenyl of 2 to 6 carbon atoms, alkynyl of 2 to 6 carbon atoms, phenyl, or benzyl;

$R^4$ is a member selected from the group consisting of H, alkyl of 1 to 6 carbon atoms, heteroalkyl of 2 to 6 carbon atoms, in which the hetero atom is oxygen, sulfur or nitrogen, alkenyl of 2 to 6 carbon atoms and alkynyl of 2 to 6 carbon atoms;

$R^5$ is

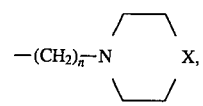

where X is O, S or $NR^7$ and $R^7$ is H or alkyl of 1 to 6 carbon atoms and n is 1, 2, 3, 4, 5, or 6;

or a pharmaceutically acceptable salt thereof.

2. A compound of claim 1 in which R and $R^6$ are H, $R^4$ is H or alkyl of 1 to 6 carbon atoms and X is O or S or a pharmaceutically acceptable salt thereof.

3. A compound of claim 1 in which R and $R^6$ are H, $R^4$ is alkyl of 1 to 3 carbon atoms and X is O or a pharmaceutically acceptable salt thereof.

4. The compound of claim 1 which is 4-[4-(2-methoxyphenyl)-piperazin-1-yl]-N-(2-morpholin-4-yl-ethyl)-2-phenyl-butyramide or a pharmaceutically acceptable salt thereof.

5. The compound of claim 1 which is 4-[4-(2-methoxyphenyl)-piperazin-1-yl]-N-(2-thiomorpholin-4-yl-ethyl)-2-phenyl-butyramide or a pharmaceutically acceptable salt thereof.

6. A pharmaceutical composition of matter comprising a compound of the formula:

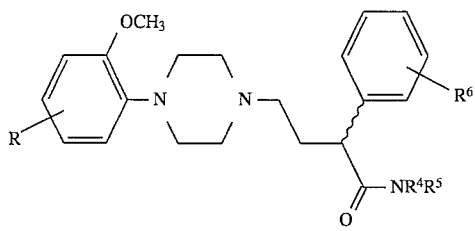

where:

R and $R^6$ are members independently selected from the group consisting of H, CN, $OR^2$, $NO_2$, $NR^2R^3$, $NR^2COR^3$, $NR^2COOR^3$, $COR^2$, $COOR^2$, $CONR^2R^3$, $SR^2$, $SOR^2$, $SO_2R^2$, $SO_2NR^2R^3$, alkyl of 1 to 6 carbon atoms, alkenyl of 2 to 6 carbon atoms, alkynyl of 2 to 6 carbon atoms, perhaloalkyl of 1 to 6 carbon atoms, and a halogen; in which $R^2$ and $R^3$ are alkyl of 1 to 6 carbon atoms, alkenyl of 2 to 6 carbon atoms, alkynyl of 2 to 6 carbon atoms, phenyl, or benzyl;

$R^4$ is a member selected from the group consisting of H, alkyl of 1 to 6 carbon atoms, heteroalkyl of 2 to 6 carbon atoms, in which the hetero atom is oxygen, sulfur or nitrogen, alkenyl of 2 to 6 carbon atoms and alkynyl of 2 to 6 carbon atoms;

$R^5$ is

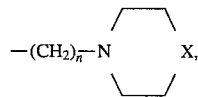

where X is O, S or $NR^7$ and $R^7$ is H or alkyl of 1 to 6 carbon atoms and n is 1, 2, 3, 4, 5, or 6;

or a pharmaceutically acceptable salt thereof.

7. A method for alleviating the symptoms of anxiety in a patient in need of treatment with an anxiolytic agent, which comprises administering, orally or parenterally, an anxiolytic amount of a compound of the formula:

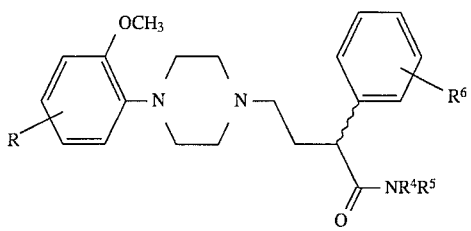

where:

R and $R^6$ are members independently selected from the group consisting of H, CN, $OR^2$, $NO_2$, $NR^2R^3$, $NR^2COR^3$, $NR^2COOR^3$, $COR^2$, $COOR^2$, $CONR^2R^3$, $SR^2$, $SOR^2$, $SO_2R^2$, $SO_2NR^2R^3$, alkyl of 1 to 6 carbon atoms, alkenyl of 2 to 6 carbon atoms, alkynyl of 2 to 6 carbon atoms, perhaloalkyl of 1 to 6 carbon atoms, and a halogen; in which $R^2$ and $R^3$ are alkyl of 1 to 6 carbon atoms, alkenyl of 2 to 6 carbon atoms, alkynyl of 2 to 6 carbon atoms, phenyl, or benzyl;

$R^4$ is a member selected from the group consisting of H, alkyl of 1 to 6 carbon atoms, heteroalkyl of 2 to 6 carbon atoms, in which the hetero atom is oxygen, sulfur or nitrogen, alkenyl of 2 to 6 carbon atoms and alkynyl of 2 to 6 carbon atoms;

$R^5$ is

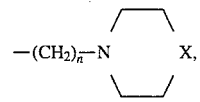

where X is O, S or $NR^7$ and $R^7$ is H or alkyl of 1 to 6 carbon atoms and n is 1, 2, 3, 4, 5, or 6;

or a pharmaceutically acceptable salt thereof.

* * * * *